(12) United States Patent
Kuiper

(10) Patent No.: US 10,716,661 B2
(45) Date of Patent: Jul. 21, 2020

(54) ACCOMMODATING INTRAOCULAR LENS WITH MENISCUS

(71) Applicant: Verily Life Sciences LLC, Mountain View, CA (US)

(72) Inventor: Stein Kuiper, Pacifica, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 16/020,661

(22) Filed: Jun. 27, 2018

(65) Prior Publication Data

US 2019/0015198 A1    Jan. 17, 2019

Related U.S. Application Data

(60) Provisional application No. 62/533,540, filed on Jul. 17, 2017.

(51) Int. Cl.
*A61F 2/16* (2006.01)

(52) U.S. Cl.
CPC .......... *A61F 2/1635* (2013.01); *A61F 2/1601* (2015.04); *A61F 2002/169* (2015.04);
(Continued)

(58) Field of Classification Search
CPC .... A61F 2/1635; A61F 2/1601; A61F 2/1648; A61F 2/1613; A61F 2/1624;
(Continued)

(56) References Cited

U.S. PATENT DOCUMENTS

| 6,117,171 A | 9/2000 | Skottun |
| 2009/0264998 A1* | 10/2009 | Mentak ................. A61F 2/1613 |
| | | 623/6.37 |

(Continued)

FOREIGN PATENT DOCUMENTS

CA    3008944 A1    3/2016

OTHER PUBLICATIONS

Bethke, Walter, "Accommodative IOLs Come into Focus", Review of Ophthalmology, Feb. 15, 2011, 4 pages.
(Continued)

*Primary Examiner* — David H Willse
*Assistant Examiner* — Tiffany P Shipmon
(74) *Attorney, Agent, or Firm* — Christensen O'Connor Johnson Kindness PLLC

(57) ABSTRACT

An intraocular lens includes an annular housing coupled to a first window to form a lensing cavity. Disposed within the lensing cavity is two immiscible liquids, including a first liquid and a second liquid which form a meniscus at an immiscibility interface between the first liquid and the second liquid within the lensing cavity. The intraocular lens includes a flexible reservoir to store a variable portion of the first liquid. The flexible reservoir is disposed about at least a portion of a periphery of the annular housing. The intraocular lens also includes at least one channel linking the flexible reservoir to the lensing cavity to permit a transfer of the first liquid between the flexible reservoir and the lensing cavity. The transfer of the first liquid changes a curvature of the meniscus to adjust optical power of the intraocular lens.

22 Claims, 5 Drawing Sheets

(52) U.S. Cl.
CPC ............... *A61F 2002/1682* (2015.04); *A61F 2230/0004* (2013.01); *A61F 2250/0003* (2013.01); *A61F 2250/0018* (2013.01); *A61F 2250/0053* (2013.01); *A61F 2250/0056* (2013.01)

(58) Field of Classification Search
CPC ........ A61F 2002/1682; A61F 2002/169; A61F 2230/0004; A61F 2250/0003; A61F 2250/0018; A61F 2250/0053; A61F 2250/0056

See application file for complete search history.

(56) References Cited

U.S. PATENT DOCUMENTS

| | | |
|---|---|---|
| 2010/0063588 A1 | 3/2010 | Park |
| 2010/0179653 A1 | 7/2010 | Argent et al. |
| 2012/0044574 A1* | 2/2012 | Pugh ............... A61F 2/1635 359/666 |
| 2012/0150292 A1 | 6/2012 | Mentak et al. |
| 2014/0180403 A1* | 6/2014 | Silvestrini ............ A61F 2/1635 623/6.4 |
| 2016/0058553 A1 | 3/2016 | Salahieh et al. |
| 2016/0235523 A1 | 8/2016 | Soda et al. |
| 2016/0331521 A1 | 11/2016 | Deboer et al. |

OTHER PUBLICATIONS

"PowerVision FluidVision Lens", Retrieved from the Internet <http://powervisionlens.com/the-problem/> PowerVision, Inc., 2014, 2 pages.
International Search Report and Written Opinion from the International Searching Authority dated Oct. 26, 2018, for International Application No. PCT/US2018/042240, filed Jul. 16, 2018, 14 pages.

\* cited by examiner

ACCOMMODATING INTRAOCULAR LENS WITH MENISCUS

CROSS-REFERENCE TO RELATED APPLICATION

This application claims the benefit of U.S. Provisional Application No. 62/533,540, filed Jul. 17, 2017, which is hereby incorporated by reference in its entirety.

TECHNICAL FIELD

This disclosure relates generally to intraocular lenses, and in particular but not exclusively, relates to mechanical accommodating intraocular lenses.

BACKGROUND INFORMATION

A cataract is a clouding of the lens in an eye which leads to a decrease in vision and can eventually lead to blindness. Surgery is needed if the cataracts are causing problems and generally results in an improved quality of life. Conventional cataract surgery involves removing the cloudy lens in an eye and replacing it with an artificial lens. However, conventional artificial lenses have a fixed focal length which may limit an individual's ability to focus on objects of varying distance.

Cataracts are most commonly due to aging, but may also occur due to trauma, be present from birth, or occur following eye surgery for other problems. More than half the people in the United States have had cataracts by the age of 80. Techniques and devices that can help individuals offset the effects of cataracts are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of apparatus, system, and method of operation for an accommodating intraocular lens with a meniscus are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
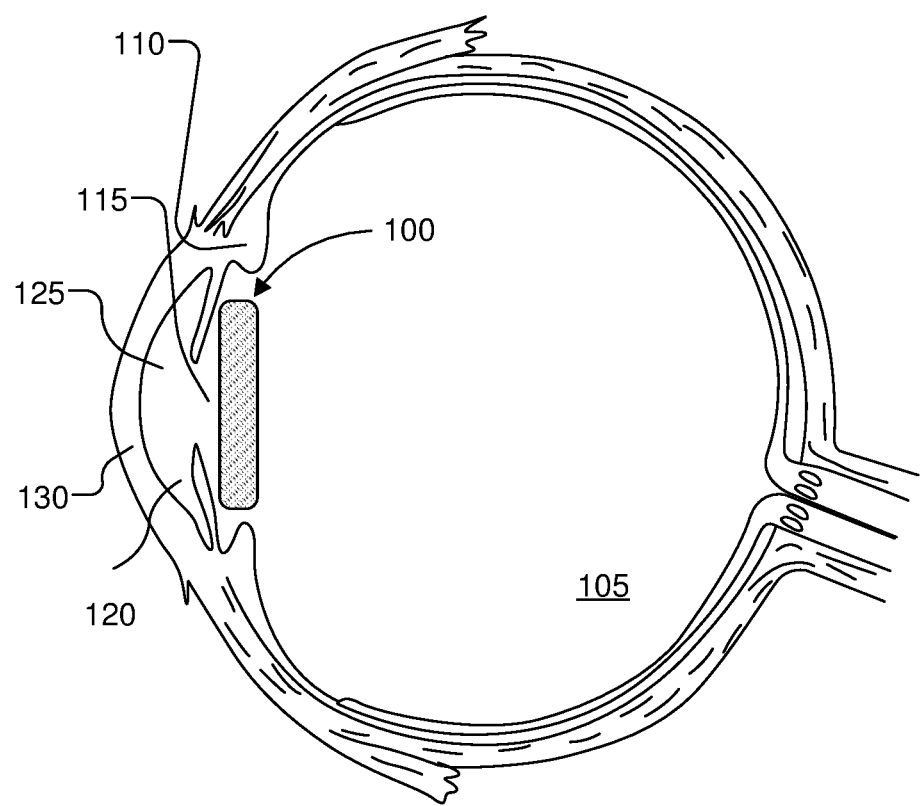
FIG. 1 is an illustration of an accommodating intraocular lens with a pinned meniscus implanted in a user's eye, in accordance with an embodiment of the disclosure.

FIG. 1 is an illustration of an accommodating intraocular lens 100 with a pinned meniscus implanted in a user's eye, in accordance with an embodiment of the disclosure. Intraocular lens 100 is configured to provide accommodation to eye 105 via the mechanical action of ciliary muscle 110. To adjust the focusing of eye 105, ciliary muscle 110 generates a force that changes the curvature of a natural eye lens. As illustrated, intraocular lens 100 is positioned where the natural eye lens would typically be located to receive the force generated by ciliary muscle 110 and in response utilize the force to adjust focusing of eye 105. Intraocular lens 100 is implanted within the posterior chamber 115 behind an iris 120 of eye 105. However, intraocular lens 100 may be implanted into other locations, as well, such as anterior chamber 125 disposed between iris 120 and cornea 130, and a portion of intraocular lens 100 positioned to receive the force generated by ciliary muscle 110. In other embodiments, the user's intent to adjust their level of accommodation may be sensed via a variety of techniques (electrical, optical, capacitive, etc.), and this sensed intent to accommodate may then be used to drive an electro-mechanical actuator for adjusting the optical power of intraocular lens 100.

Figure 2A:
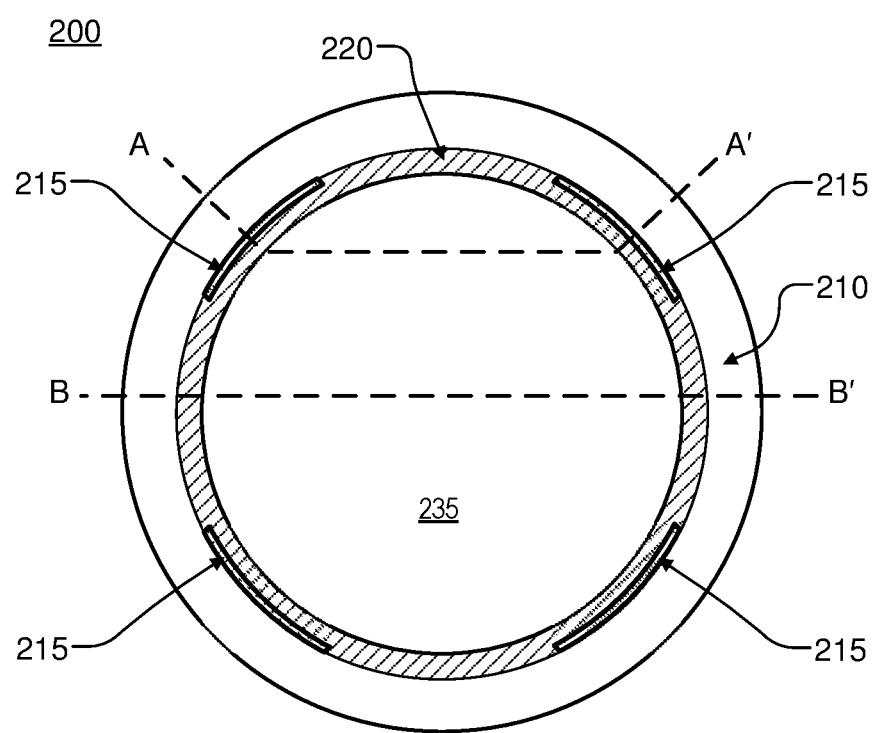
FIG. 2A is a top view illustration of a mechanical accommodating intraocular lens with a pinned meniscus, in accordance with an embodiment of the disclosure.

FIG. 2A is a top view illustration of a mechanical accommodating intraocular lens 200 with a pinned meniscus, in accordance with an embodiment of the disclosure. Intraocular lens 200 is one possible implementation of intraocular lens 100. Intraocular lens 200 may be implanted in a user's eye in a similar manner as described in regards to intraocular lens 100 of FIG. 1. The illustrated embodiment of intraocular lens 200 includes flexible reservoir 210, channels 215, annular housing 220, and lensing cavity 235.

Flexible reservoir 210 is disposed about at least a portion of a periphery of annular housing 220. Flexible reservoir 210 is illustrated as a ring-shaped reservoir that surrounds annular housing 220 and lensing cavity 235. In the illustrated embodiment, annular housing 220 integrally forms a portion of the sidewall of flexible reservoir 210. However, it is appreciated that flexible reservoir 210 may also comprise one or more separated reservoirs that are disposed about different portions of the periphery of annular housing 220. Annular housing 220 is disposed between flexible reservoir 210 and lensing cavity 235. At least one opening within annular housing 220 may form channel 215. Channels 215 extend through annular housing 220 to form at least one slit coupled between flexible reservoir 210 and lensing cavity 235.

Figure 2B:
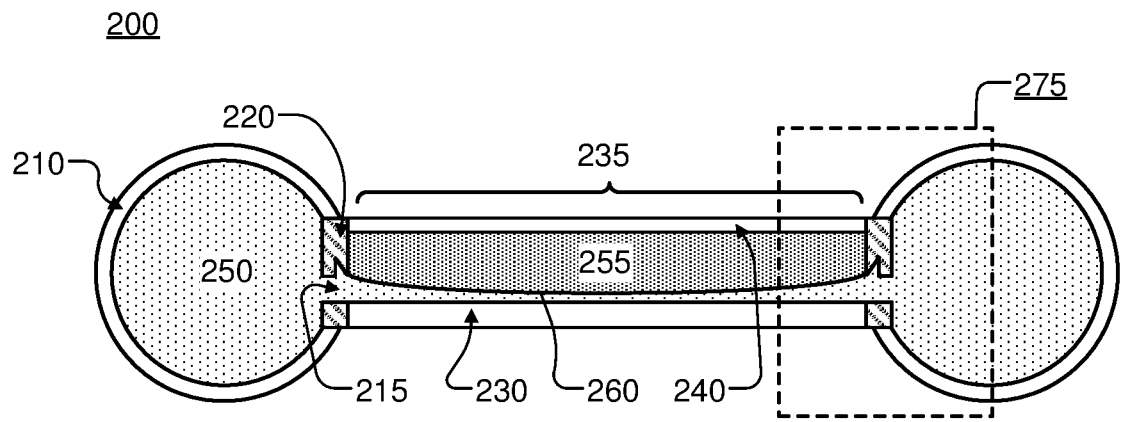
FIG. 2B is a cross sectional illustration of a mechanical accommodating intraocular lens with a pinned meniscus taken along line A-A' shown in FIG. 2A, in accordance with an embodiment of the disclosure.

FIG. 2B is a cross sectional illustration of mechanical accommodating intraocular lens 200 with a pinned meniscus taken along line A-A' shown in FIG. 2A, in accordance with an embodiment of the disclosure. FIG. 2B illustrates flexible reservoir 210, channel 215, annular housing 220, first window 230, lensing cavity 235, second window 240, first liquid 250, second liquid 255, and meniscus 260 of intraocular lens 200.

Annular housing 220 is coupled to first window 230 to form lensing cavity 235. Disposed within lensing cavity 235 is two immiscible liquids, including first liquid 250 and second liquid 255. The two immiscible liquids form a meniscus 260 at an immiscibility interface between first liquid 250 and second liquid 255 within lensing cavity 235. Flexible reservoir 210 stores a variable portion of first liquid 250. Channel 215 links flexible reservoir 210 to lensing cavity 235 to permit a transfer of first liquid 250 between flexible reservoir 210 and lensing cavity 235. In one embodiment, one or more channels 215 may be coupled to flexible reservoir 210 via a tube, or other external channel, which permits remote placement of flexible reservoir 210 from annular housing 220. Furthermore, an actuator or pumping mechanism (e.g., electro-mechanical, electrostatic, etc.) may be used to drive transfer of first liquid 250 into or out of lensing cavity 235.

Meniscus 260 forms a lens that has adjustable optical power based at least in part on a curvature of meniscus 260. Meniscus 260 provides optical power because it represents an interface between two mediums (first liquid 250 and second liquid 255) having different refractive indices. First liquid 250 has a first refractive index which is different than a second refractive index of second liquid 255. Thus, meniscus 260 provides optical power to light propagating through lensing cavity 235 that is incident on meniscus 260. The optical power of meniscus 260 is adjustable when the curvature of meniscus 260 changes in response to a transfer of first liquid 250 between flexible reservoir 210 and lensing cavity 235. Furthermore, in some embodiments, a first density of first liquid 250 is substantially equal to a second density of second liquid 255. By having comparable densities, a shape of meniscus 260 may be spherical and independent of the orientation of intraocular lens 200 with respect to gravity. The spherical shape of meniscus 260 provided by intraocular lens 200 reduces optical aberrations compared to a non-spherical shape such as formed by deforming an elastic membrane.

Figure 2C:
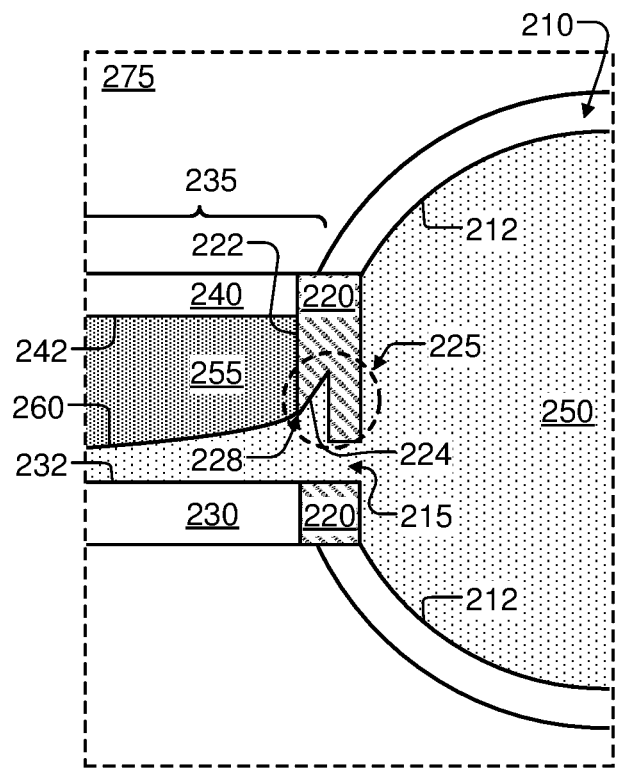
FIG. 2C is a cross sectional illustration of a sub-section of the mechanical accommodating intraocular lens with a pinned meniscus shown in FIG. 2B, in accordance with an embodiment of the disclosure.

FIG. 2C is a cross sectional illustration of sub-section 275 of mechanical accommodating intraocular lens 200 shown in FIG. 2B, in accordance with an embodiment of the disclosure. FIG. 2C provides a closer view of sub-section 275 of intraocular lens 200 in order to adequately describe the interaction between the two immiscible fluids and the various surfaces of intraocular lens 200.

Sub-section 275 of intraocular lens 200 includes flexible reservoir 210 (including reservoir surface 212), channel 215, annular housing 220 (including first side 222, indent surface 224, pinning structure 225, and sharp edge 228), first window 230 (including first surface 232), lensing cavity 235, second window 240 (including second surface 242), first liquid 250, second liquid 255, and meniscus 260.

The surfaces of intraocular lens 200 are specifically designed to aid in maintaining the formation of meniscus 260 within lensing cavity 235. In general, though not required, as illustrated in FIG. 2C, if a surface interfaces with first liquid 250, the same surface may be chemically treated or have a specific morphological structure to attract first liquid 250 or repel second liquid 255. Similarly, if a surface interfaces with second liquid 255, the same surface may be chemically treated or have a specific morphological structure to attract second liquid 255 or repel first liquid 250.

In one embodiment, reservoir surface 212 of flexible reservoir 210 and first surface 232 of first window 230 interface with first liquid 250. Reservoir surface 212 and first surface 232 may be adapted to attract first liquid 250 and/or repel second liquid 255. In this context, a surface attracting first liquid 250 (e.g. reservoir surface 212, indent surface 224, and/or first surface 232) signifies that it is energetically favorable for first liquid 250 to wet (e.g. spread out, cover, or interact with) said surface. In other words, it is more energetically favorable for molecules of first liquid 250 to interact with said surface than other molecules of first liquid 250. A surface repelling second liquid 255 signifies that it is energetically unfavorable for second liquid 255 to wet said surface. In the same or another embodiment, first side 222 of annular housing 220 and second surface 242 of second window 240 interface with second liquid 255. First side 222 and second surface 242 may be adapted to attract second liquid 255 and/or repel first liquid 250.

Various methods may be used in order to achieve the desired attractive and/or repulsive properties of the surfaces that interface with first liquid 250 and second liquid 255 of intraocular lens 200. These methods may be directly related to the composition of first liquid 250 and second liquid 255.

In one embodiment, first liquid 250 has a biocompatible oil based composition (e.g. long-chained hydrocarbons such as silicone oil) and second liquid 255 has a water based composition (e.g. saline). First side 222 and second surface 242 are chemically treated to form an underwater super oleophobic surface. Upon exposure to second liquid 255, first side 222 and second surface 242 become super oleophobic surfaces and repel first liquid 250.

In another embodiment, first liquid 250 has a biocompatible oil based composition and second liquid has a water based composition as previously described. First side 222 may be chemically treated to attract second liquid 255. For example, in one embodiment, annular housing 220 comprises a biocompatible polymeric material containing various hydrocarbon groups. First side 222 may be exposed to an oxygen plasma to introduce various hydroxyl groups to first side 222 which would make first side 222 substantially hydrophilic. Alternatively, or additionally, first side 222 may be treated with various surfactants or other adlayers to generate a hydrophilic surface or oleophobic surface at first side 222.

In the same, or another embodiment, the morphological structure of the surfaces within intraocular lens 200 may be configured to provide the desired attraction and repulsion properties. Annular housing 220 may include pinning structure 225. Pinning structure 225 surrounds meniscus 260 and pins a perimeter of meniscus 260 to first side 222 of annular housing 220. In particular, a width of pinning structure 225 tapers to form sharp edge 228 within lensing cavity 235. Sharp edge 228 subsequently pins the perimeter of meniscus 260 to a fixed position of first side 222. The change in geometry introduced by sharp edge 228 creates an abrupt change in surface energy at a fixed position on first side 222. The sudden change in surface energy at first side 222 makes it energetically unfavorable for meniscus 260 to extend beyond sharp edge 228. An abrupt change in surface roughness may also provide a desirable change in surface energy. For example, the surface roughness of indent surface 224 may be sufficiently high to repel second liquid 255.

Figure 2D:
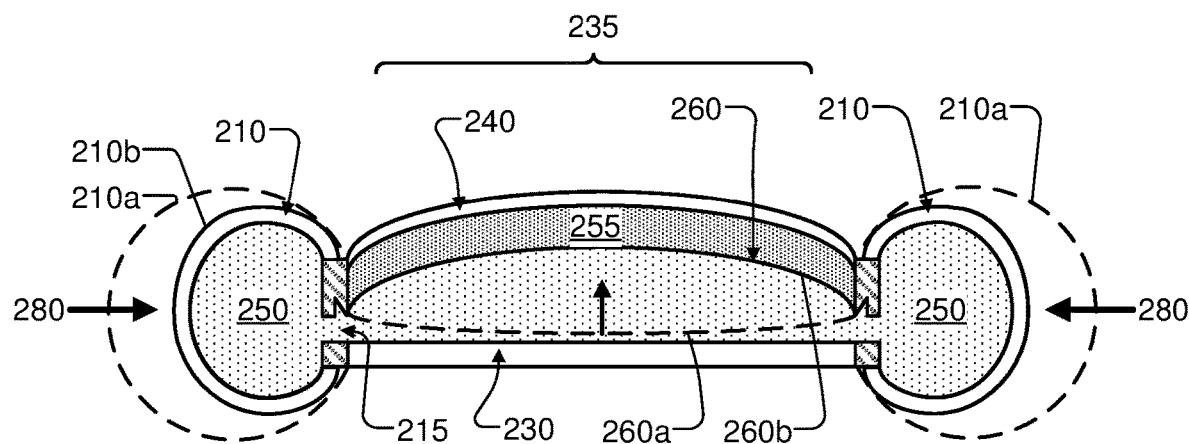
FIG. 2D is a cross sectional illustration of a mechanical accommodating intraocular lens with a pinned meniscus under the application of an external force, in accordance with an embodiment of the disclosure.

FIG. 2D is a cross sectional illustration of a mechanical accommodating intraocular lens 200 under the application of an external force (e.g. contraction of the ciliary muscle, an electro-mechanical actuator, etc.), in accordance with an embodiment of the disclosure. FIG. 2D illustrates the response of intraocular lens 200 to external force 280 applied to flexible reservoir 210.

Intraocular lens 200 operates under the principle of liquid displacement. In response to external force 280 being applied to flexible reservoir 210, a portion of first liquid 250 is transferred between flexible reservoir 210 and lensing cavity 235. The transfer of the portion of first liquid 250 changes a curvature of meniscus 260 to adjust optical power of intraocular lens 200.

In the illustrated embodiment, external force 280 is a compressive force that reduces a volume of flexible reservoir 210 from a first volume 210a to a second volume 210b. Intraocular lens 200 responds to the application of external force 280 by transferring a portion of first liquid 250 from flexible reservoir 210 to lensing cavity 235 via channel 215. The transferred portion of first liquid 250 has a volume that is the difference between first volume 210a and second volume 210b of flexible reservoir 210. Since the perimeter of meniscus 260 is pinned to a fixed position on pinning structure 225, the curvature of meniscus 260, changes from first curvature 260a to second curvature 260b to accommodate the volume of the transferred portion of first liquid 250. The change in curvature of meniscus 260 adjusts the optical power provided by intraocular lens 200 because the radius of curvature of meniscus 260 changes in response to the transfer of a portion of first liquid 250. In other words, the optical power of intraocular lens 200 can be finely tuned based on the magnitude and direction of external force 280. While the illustrated embodiment details the response of intraocular lens 200 to a compressive force, it is appreciated that other types of forces may be applied to flexible reservoir 210 (e.g. a tensile force that increases the volume of flexible reservoir 210 to transfer a portion of second liquid 255 from lensing cavity 235 to flexible reservoir 210, electrostatic force, etc.), and that intraocular lens 200 will respond in accordance with the teachings of the present disclosure.

In addition to the curvature of meniscus 260 changing in response to the application of external force 280, a shape of second window 240 may also change appropriately to accommodate the transferred portion of first liquid 250. Second window 240 may have a greater flexibility or elasticity than first window 230 such that second window 240 changes shape or deforms in response to external force 280 while first window 230 remains substantially planar or fixed in shape. The change in shape of second window 240 may result in a non-planar or non-spherical shape. It may be desirable to prevent the shape of second window 240 from introducing optical power or aberrations when implanted within an eye. In such a case, the refractive index of liquid 255 is substantially equal to the surrounding vitreous liquid of the eye, such that deformation of window 240 does not impart optical power. An advantage hereof is that non-spherical deformation of window 240 does not lead to optical aberrations.

Figure 2E:
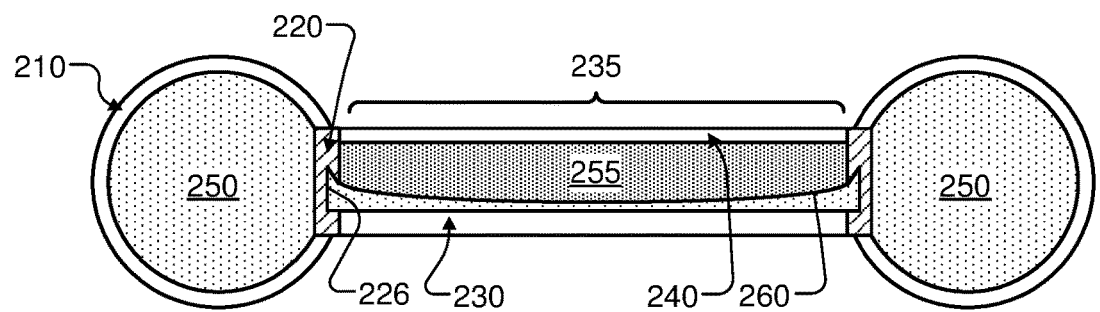
FIG. 2E is a cross sectional illustration of the mechanical accommodating intraocular lens with a pinned meniscus taken along line B-B' shown in FIG. 2A, in accordance with an embodiment of the disclosure.

FIG. 2E is a cross sectional illustration of a mechanical accommodating intraocular lens 200 taken along line B-B' shown in FIG. 2A, in accordance with an embodiment of the disclosure. Line B-B' shown in FIG. 2A illustrates a cross-section of intraocular lens 200 that does not extend through channels 215.

In the illustrated embodiment, annular housing 220 includes support structure 226. Support structure 226 is coupled between first window 230 and second window 240 to provide structural support to intraocular lens 200. In particular, support structure 226 provides rigidity to lensing cavity 235 such that a thickness of the perimeter of lensing cavity 235 is consistent about its periphery.

Figure 3:
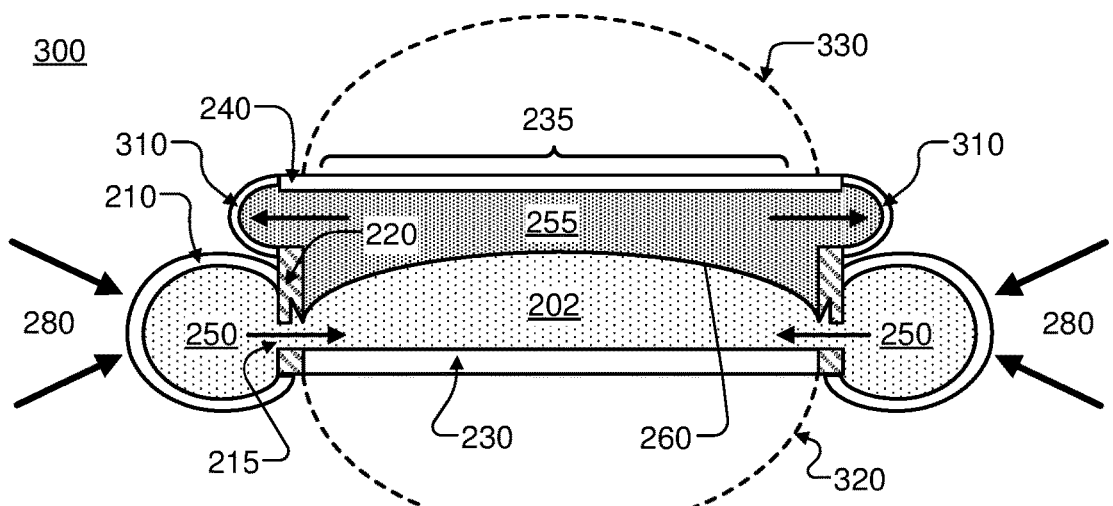
FIG. 3 is a cross sectional illustration of a mechanical accommodating intraocular lens with a pinned meniscus, in accordance with an embodiment of the disclosure.

FIG. 3 is a cross sectional illustration of a mechanical accommodating intraocular lens 300 with a pinned meniscus, in accordance with an embodiment of the disclosure.

Intraocular lens 300 is another possible implementation of intraocular lens 100, with similar features as intraocular lens 200 except intraocular lens 300 includes flexible member 310, first lens 320 (optional), and second lens 330 (optional). In particular, intraocular lens 300 is similar to intraocular lens 200 illustrated in FIG. 2D. However, intraocular lens 300 responds to external force 280 differently than intraocular lens 200. Flexible member 310 is at least partially disposed between second window 240 and a perimeter of meniscus 260. Flexible member 310 may permit second window 240 to be flexibly attached to annular housing 220.

As illustrated, intraocular lens 300 responds to external force 280 applied to flexible reservoir 210 by transferring a portion of first liquid 250 from flexible reservoir 210 to lensing cavity 235 via channel 215. To accommodate for the added volume of the transferred portion of first liquid 250 within lensing cavity 235, flexible member 310 changes shape. The change in shape of flexible member 310 may be elastic deformation that returns to a rest state upon the cessation of external force 280. Alternatively, or additionally, flexible member 310 may comprise a bellows structure to permit a distance between second window 240 and a perimeter of meniscus 260 to change in response to the transfer of first liquid 250.

Intraocular lens 300 may include a first lens 320 disposed across a first external surface of first window 230 to provide a baseline optical power. Similarly, second lens 330 may be disposed across a second external surface of second window 240 to also provide baseline optical power of intraocular lens 300. While first lens 320 and second lens 330 are discussed in relationship to intraocular lens 300 it is appreciated that the other intraocular lens discussed (e.g. intraocular lens 100 and intraocular lens 200) within this disclosure may also include one or more of these lenses to provide a baseline optical power.

Figure 4:
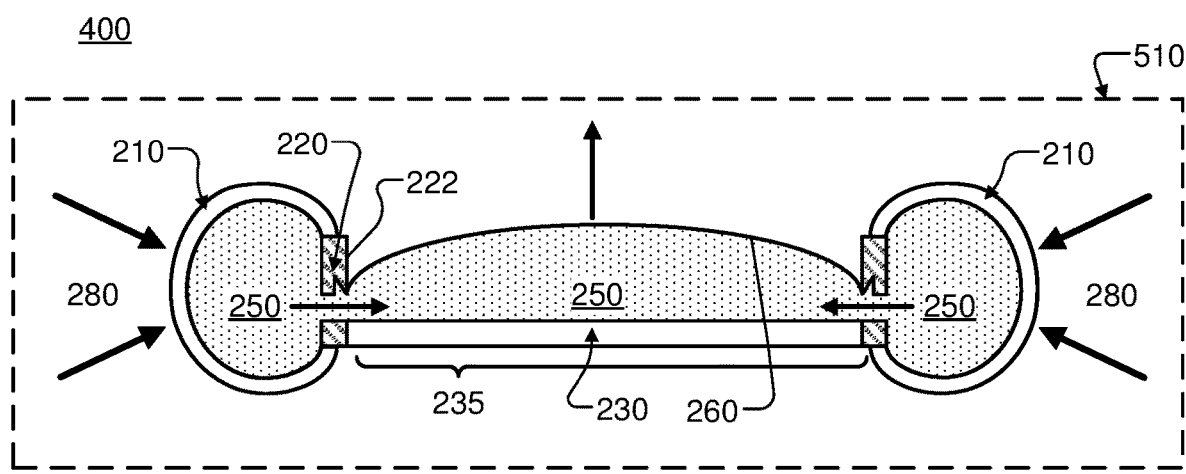
FIG. 4 is a cross sectional illustration of a mechanical accommodating intraocular lens with a pinned meniscus, in accordance with an embodiment of the disclosure.

FIG. 4 is a cross sectional illustration of a mechanical accommodating intraocular lens 400 with a pinned meniscus, in accordance with an embodiment of the disclosure. FIG. 4 includes intraocular lens 400, external force 280, and medium 510. Intraocular lens 400 includes flexible reservoir 210, channel 215, annular housing 220 (including first side 222), first window 230, lensing cavity 235, first liquid 250, and meniscus 260.

Intraocular lens 400 is similar to intraocular lens 200 illustrated in FIG. 2D. However, lensing cavity 235 of intraocular lens 400 of FIG. 4 is not sealed. Rather, intraocular lens 400 does not include a second window and is thus directly exposed to medium 510. In one embodiment, intraocular lens 400 is implanted in a user's eye (as illustrated in FIG. 1), and medium 510 is vitreous fluid of the capsular sac. Even though intraocular lens 400 is not sealed, meniscus 260 is maintained at least in part due to medium 510 being immiscible with first liquid 250. In one embodiment, first liquid 250 is a long hydrocarbon chain based silicone oil that is immiscible with vitreous fluid. Furthermore, a first side 222 of annular housing 220 may include a chemical treatment or morphological structure that attracts medium 510 or repels first liquid 250. Additionally, or alternatively, the surfaces of intraocular lens 400 that are illustrated as interfacing with first liquid 250 may include a chemical treatment or morphological structure that attracts first liquid 250 or repels medium 510, in accordance with an embodiment of the disclosure. Furthermore, first liquid 250 may contain a surfactant that is insoluble in medium 510. This surfactant may reduce the surface energy of meniscus 260 and with that prevent fouling of meniscus 260 caused by cell debris floating around in medium 510.

Intraocular lens 400 may include a removable cover (sticker) that could be used as a temporary window to protect first liquid 250 during the insertion of intraocular lens 400 into a user's eye. Alternatively, intraocular lens 400 may include a thin membrane to seal first liquid 250 within intraocular lens 400. Subsequently, upon the insertion of intraocular lens 400 into a user's eye, the thin membrane may be punctured or removed to form meniscus 260.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An intraocular lens, comprising:
   an annular housing coupled to a first window to form a lensing cavity, wherein two immiscible liquids, including a first liquid and a second liquid, form a meniscus at an immiscibility interface between the first liquid and the second liquid within the lensing cavity when the intraocular lens is implanted into an eye;
   a flexible reservoir disposed about at least a portion of a periphery of the annular housing, wherein the flexible reservoir stores a variable portion of the first liquid; and
   at least one channel linking the flexible reservoir to the lensing cavity to permit a transfer of the first liquid between the flexible reservoir and the lensing cavity, wherein a curvature of the meniscus and an optical power of the intraocular lens are adjustable in response to transferring the first liquid through the at least one channel,
   wherein the annular housing includes a pinning structure surrounding the meniscus that pins a perimeter of the meniscus to a fixed position on the annular housing.

2. The intraocular lens of claim 1, wherein the flexible reservoir is adapted to cause the first liquid to transfer between the flexible reservoir and the lensing cavity in response to an external force applied to the flexible reservoir.

3. The intraocular lens of claim 1, wherein at least one opening within the pinning structure forms the at least one channel.

4. The intraocular lens of claim 3, wherein the pinning structure comprises an abrupt change in surface energy.

5. The intraocular lens of claim 3, wherein a cross-sectional shape of the pinning structure tapers to form a sharp edge that pins the perimeter of the meniscus to the fixed position.

6. The intraocular lens of claim 3, wherein an abrupt change in surface roughness of the pinning structure pins the perimeter of the meniscus to the fixed position.

7. The intraocular lens of claim 3, wherein the first liquid interfaces with a first side of the pinning structure, and wherein at least a first portion of the first side is treated to attract the first liquid or repel the second liquid.

8. The intraocular lens of claim 3, further comprising:
   a second window coupled to the annular housing, wherein the meniscus and the lensing cavity are disposed between the first window and the second window.

9. The intraocular lens of claim 8, wherein an inner surface of the second window interfaces with the second liquid within the lensing cavity, and wherein the inner surface is treated to attract the second liquid or repel the first liquid.

10. The intraocular lens of claim 8, wherein the annular housing further includes a flexible member, wherein the flexible member is at least partially disposed between the second window and the meniscus.

11. The intraocular lens of claim 10, wherein the flexible member is a bellows structure surrounding the lensing cavity, and wherein the bellows structure permits a distance between the second window and a perimeter of the meniscus to change in response to the transfer of the first liquid.

12. The intraocular lens of claim 8, wherein the second window is flexible, and wherein a shape of the second window changes in response to the transfer of the first liquid.

13. The intraocular lens of claim 8, further comprising a baseline lens disposed across at least one of the first window or the second window.

14. The intraocular lens of claim 1, wherein a first density of the first liquid is substantially equal to a second density of the second liquid, and wherein a first refractive index of the first liquid is different than a second refractive index of the second liquid.

15. The intraocular lens of claim 1, wherein the first liquid comprises water and the second liquid comprises oil.

16. The intraocular lens of claim 1, wherein the first liquid has a refractive index that is substantially equal to a vitreous liquid of a human eye.

17. An intraocular lens, comprising:
   an annular housing;
   first and second windows disposed on opposing sides of the annular housing to define a lensing cavity with the annular housing;
   two immiscible liquids, including a first liquid and a second liquid, forming a meniscus at an immiscibility interface between the first liquid and the second liquid disposed within the lensing cavity;
   a reservoir for storing a variable portion of the first liquid; and
   a channel linking the reservoir to the lensing cavity to permit a transfer of the first liquid between the reservoir and the lensing cavity, wherein a curvature of the meniscus and an optical power of the intraocular lens changes in response to transferring the first liquid, wherein the annular housing includes a pinning structure surrounding the meniscus that pins a perimeter of the meniscus to a fixed position on the annular housing.

18. The intraocular lens of claim 17, wherein the reservoir comprises a flexible reservoir adapted to cause the first liquid to transfer between the flexible reservoir and the lensing cavity in response to an external force applied to the flexible reservoir.

19. The intraocular lens of claim 18, wherein the flexible reservoir forms a ring-shape around the annular housing and wherein the annular housing integrally forms a portion of the flexible reservoir.

20. The intraocular lens of claim 17, wherein at least one opening within the pinning structure forms at least a portion of the channel.

21. The intraocular lens of claim 20, wherein a cross-sectional shape of the pinning structure tapers to form a sharp edge that pins the perimeter of the meniscus to the fixed position.

22. The intraocular lens of claim 20, wherein the pinning structure includes an indent surface having an abrupt change in surface roughness of the pinning structure that pins the perimeter of the meniscus to the fixed position.

\* \* \* \* \*